United States Patent [19]
Iguchi et al.

[11] Patent Number: 5,811,531
[45] Date of Patent: Sep. 22, 1998

[54] ABSORBENT WITH STABILITY AGAINST SALTS AND PROCESS FOR PRODUCTION THEREOF

[75] Inventors: Kazuhiko Iguchi; Shingo Mukaida; Kenji Tanaka, all of Kyoto, Japan

[73] Assignee: Sanyo Chemical Industries, Ltd., Kyoto, Japan

[21] Appl. No.: 436,177

[22] Filed: May 9, 1995

Related U.S. Application Data

[63] Continuation of PCT/JP93/01526, Oct. 21, 1993.

[30] Foreign Application Priority Data

Nov. 18, 1992 [JP] Japan .................................. 4-333684

[51] Int. Cl.$^6$ .............................. B01J 20/24; B01J 20/26; B01J 20/28; B01J 20/30
[52] U.S. Cl. ................................. 536/1.11; 536/2; 536/3; 536/21; 536/114
[58] Field of Search .................................. 536/1.11, 2, 3, 536/21, 114; 525/54.3, 54.31

[56] References Cited

U.S. PATENT DOCUMENTS

| | | | |
|---|---|---|---|
| 4,051,086 | 9/1977 | Reid | 524/47 |
| 4,076,663 | 2/1978 | Masuda et al. | 524/47 |
| 4,734,478 | 3/1988 | Tsubakimoto et al. | 527/300 |
| 5,470,964 | 11/1995 | Qin | 536/20 |

FOREIGN PATENT DOCUMENTS

| | | |
|---|---|---|
| 0 454 497 | 10/1991 | European Pat. Off. . |
| 2 305 452 | 3/1976 | France . |
| 2 345 470 | 2/1977 | France . |
| A-56-005137 | 1/1981 | Japan . |
| A-56-005138 | 1/1981 | Japan . |
| 58-44018 | 9/1983 | Japan . |
| 61-094655 | 5/1986 | Japan . |
| 1-17411 | 3/1989 | Japan . |

OTHER PUBLICATIONS

European Search Report for Application No. PCT/JP93/01526 dated Jan. 10, 1994.

Copy of Supplementary European search Report dated Jan. 8, 1996.

*Primary Examiner*—Nathan M. Nutter
*Attorney, Agent, or Firm*—Merchant, Gould, Smith, Edell, Welter & Schmidt, P.A.

[57] ABSTRACT

Absorbents of the present invention can be obtained by reacting the vicinity of the surface of (A) polysaccharide particles with a (B) crosslinking agent having at least two functional groups which can react with the polysaccharides such as polyglycidyl ether compounds, polyhydric alcohol compounds or polyamine compounds by means of treating the (A) polysaccharide particles with the (B) crosslinking agent and an aqueous solution of a (C) water soluble compound while heated. The obtained absorbents exhibit excellent absorbing ability even to a high concentrated salt solution and also are well biodegradable.

8 Claims, No Drawings

ABSORBENT WITH STABILITY AGAINST SALTS AND PROCESS FOR PRODUCTION THEREOF

This application is a continuation of PCT/JP93/01526 Oct. 21, 1993.

TECHNICAL FIELD

This invention relates to absorbents having excellent absorbency against a highly concentrated aqueous solution of salts and production processes thereof, and more specifically, absorbents obtainable by reacting the surface of polysaccharide particles with a crosslinking agent and production processes thereof.

BACKGROUND ART

Conventionally high water absorbent resins have been applied broadly to hygienic materials such as sanitary napkins, disposable diapers and the like, or water retaining materials for soil. As the examples of such high water absorbent resins, crosslinked polyacrylic acid salt, self-crosslinked polyacrylic acid salt, crosslinked copolymers of starch-grafted acrylic acid salt, copolymers of vinyl alcohol-acrylic acid salt, hydrolyzates of crosslinked copolymers of acrylamide, neutralized copolymers of crosslinked isobutylene-maleic acid anhydride, and crosslinked carboxymethylcellulose salt are known.

While these absorbents exhibit high absorbency against pure water, they have a disadvantage in that their absorbency against a salt solution is remarkably low.

To solve the disadvantage, a method to crosslink by heating polysaccharide containing uronic acid or salts thereof as a unit component to change the state to be insoluble (the Japanese Patent Laid Open Application No. 5137/1981), a method to dissolve polysaccharide containing uronic acid or salts thereof as a unit component in a large amount of a solvent, and add a crosslinking agent and optionally water-soluble monomer to cause reaction, or a method to dissolve polysaccharide in a large amount of a solvent, and add a crosslinking agent, an etherification agent and optionally water-soluble monomer to cause reaction (the Japanese Patent Laid Open Application No. 5138/1981) have been proposed.

However, since the crosslinking reaction is conducted by dissolving polysaccharide in a large amount of a solvent in such methods, the polysaccharides are crosslinked uniformly to the inside. Therefore although a relatively good absorbing ability can be expected against a dilute solution of salt such as physiolosical saline solution, there are problems that in absorbing or gelling a high concentrated salt solution such as mud containing sea water dug out from the soil near a sea, such method cannot be applied or much absorbent should be used due to a small absorbing capacity.

The inventors of the present invention studied the above mentioned problems and earnestly studied to obtain an absorbent having a good absorbing ability against a high concentrated salt solution to accomplish the present invention.

The object of the present invention is to provide absorbents having a good absorbing ability against a high concentrated salt solution and the manufacturing process thereof.

DISCLOSURE OF INVENTION

The present invention relates to an absorbent comprising a resin obtained by reacting the surface of (A) polysaccharide particles with a (B) crosslinking agent having at least two functional groups which can react with the (A) polysaccharide particles.

Further, the present invention relates to a manufacturing process of an absorbent comprising a resin obtained by reacting the surface of (A) polysaccharide particles with a (B) crosslinking agent having at least two functional groups which can react with the (A) polysaccharide particles characterized by treating the (A) polysaccharide particles with an aqueous solution of the (B) crosslinking agent and a (C) water-soluble compound.

BEST MODE FOR CARRYING OUT THE INVENTION

Examples of (A) polysaccharide particles include alginic acid or salts thereof, pectin, tragacanth gum, gum arabic, heparin, xanthan gum, locust bean gum, guar gum, mannan, glucomannan, carrageenan, cellulose, amylose, amylopectin.

These polysaccharides can be chemically treated by methods such as carboxy alkyl etherification (such as carboxy methylation) and hydroxy alkyl etherification (such as hydroxy ethylation). Further, adducts of alkylene oxide (such as ethylene oxide and/or propylene oxide) can be included.

The above-mentioned examples of polysaccharide particles can be used in combination of two or more.

Since water-soluble polysaccharides having an uronic acid group and/or a group of salts thereof have a good absorbing ability against a high concentrated salt solution, they are preferable among these examples, especially pectin and xanthan gum are particularly preferable. "An uronic acid group" herein refers to a carboxyl group formed by oxidation of an aldehyde group or a primary alcohol group of a monosaccharide. Therefore since the carboxyl group is directly bonded to the saccharide skeleton, it is very different from the carboxyl methylated polysaccharides such as CMC (carboxy methyl cellulose) in terms of the structure and the salt resistance property.

Examples of unit components of such saccharides having a uronic group include β-D-glucuronic acid, α-L-glucuronic acid, α-D-mannuronic acid, α-D-galacturonic acid, α-L-iduronic acid, 4-0-methyl-D-glucuronic acid and the like.

Examples of salts of a uronic acid include alkali metal salts (such as sodium salts, potassium salts), ammonium salts, amine salts (such as alkyl amines having carbon atoms of total 1 to 12 in alkyl groups, alkanol amines having carbon atoms of total 1 to 12 in alkanol groups). Among these salts, the alkali metal salts are preferable.

The shape of the (A) polysaccharide particles is not especially limited. Any of pearly, lamellar, lumpy, amorphous, and fine powdery shapes can be used. Further, the particle size is not particularly limited but in general, it is about 10 to 1,000 $\mu$m.

In the present invention, the (B) crosslinking agent is a compound having at least two functional groups which can react with the (A) polysaccharides, for example, a compound having at least two functional groups which can react with carboxylic acid group and/or a hydroxyl group and such compound can be used without limitation, particularly a water-soluble crosslinking agent is preferable.

Examples of the (B) crosslinking agents include polyglycidyl ether compounds, haloepoxy compounds, polyaldehyde compounds, polyhydric alcohol compounds, polyamine compounds and polyisocyanate compounds. These compounds can be used in a combination of two or more.

Examples of polyglycidyl ether compounds include ethylene glycol diglycidyl ether, propylene glycol diglycidyl ether, glycerol-1,3-diglycidyl ether, glycerol triglycidyl ether, polyethylene glycol diglycidyl ether and 1,6-hexanediol diglycidyl ether.

Examples of haloepoxy compounds include epichlorohydrin and α-methyl epichlorohydrin.

Examples of polyaldehyde compounds include glutaraldehyde and glyoxal.

Examples of polyhydric alcohol compounds include glycerol, ethylene glycol, diethylene glycol, propylene glycol, polyethylene glycol, polypropylene glycol, diethanol amine and triethanol amine.

Examples of polyamine compounds include ethylene diamine, diethylene triamine, triethylene tetramine, tetraethylene pentamine, polyamide resin as a reactant of polyamine and aliphatic polybasic acid and polyamide polyamine epichlorohydrin resin.

Examples of polyisocyanate compounds include tolylene diisocyanate, hexamethylene diisocyanate.

Among these examples of the (B) crosslinking agents, polyglycidyl ether compounds, polyhydric alcohol compounds and polyamine compounds are preferable. Due to lower reaction temperature and economical energy cost, ethylene glycol diglycidyl ether, propylene glycol diglycidyl ether, glycerol-1,3-diglycidyl ether, glycerol triglycidyl ether and polyamide polyamine epichlorohydrin resins are particularly preferable.

In the present invention, the ratio of the (B) crosslinking agent to the (A) polysaccharide particles varies depending upon the kind of the (A) polysaccharide particles and the (B) crosslinking agent, and the desired performance of the water absorbent resin to be obtained, but it is generally in the range of from 0.01 to 5 parts by weight of (B) to 100 parts by weight of (A), preferably from 0.05 to 3 parts by weight of (B), more preferably from 0.1 to 2 parts by weight of (B). If the amount of (B) is less than 0.01 parts by weight, the crosslinking effects cannot be attained sufficiently, whereas if the amount exceeds 5 parts by weight, the crosslinking density becomes so large that the water absorbency will be lowered.

The absorbent of the present invention needs to have a structure that the vicinity of the surface of the (A) polysaccharide particles is crosslinked but the inside of the polysaccharide particles is scarcely crosslinked. For that reason, the crosslinking procedure in the production process of this invention is preferably conducted with the presence of a (C) water-soluble compound.

A (C) water-soluble compound in this invention is virtually inert to both (A) and (B) and comprises at least one from the group consisting of (a) alkylene oxide adducts of monofunctional alcohol, (b) monovalent salts of organic acid, (c) lactams, (d) monohydric alcohols and (e) ketones.

Examples of (a) alkylene oxide adducts of monohydric alcohol include ethylene oxide adducts of methanol, ethylene oxide adducts of ethanol, ethylene oxide adducts of butylalcohol, propylene oxide adducts of methanol, and ethylene oxide/propylene oxide (block or random) adducts of methanol. The number of carbon atoms of the monohydric alcohols is preferably from 1 to 5, and the number of carbon atoms of the alkylene groups of the alkylene oxide is preferably from 2 to 4.

Examples of (b) monovalent salts of organic acid include alkali metal salts, amine salts and ammonium salts of an organic acid, such as sodium acetate, potassium acetate, ammonium acetate, sodium propionate, potassium propionate, ammonium propionate, sodium lactate and potassium lactate. As an organic acid, monobasic acids having 2 to 6 carbon atoms are preferable. "A monovalent salt" herein refers to a salt having a monovalent cation as the cation to constitute the salt.

Examples of (c) lactams include β-propiolactam, γ-butyrolactam, δ-valerolactam and ε-caprolactam. The lactams having 3 to 9 carbon atoms are preferable.

Examples of (d) monohydric alcohols include monohydric alcohols having 1 to 4 carbon atoms such as methanol, ethanol, isopropanol.

Examples of (e) ketones include ketones having 1 to 5 carbon atoms such as acetone and methyl ethyl ketone.

Among those described as the examples of (C) water soluble compounds, ethylene oxide adducts of monohydric alcohol, alkali metal salts of an organic acid, and cyclic lactams having 4 to 8 carbon atoms are preferable. Particularly preferable are ethylene oxide 2 to 10 mols adducts of monohydric alcohol, alkali metal salt of propionic acid and ε-caprolactam.

In the present invention, the concentration of the aqueous solution of a (C) water soluble compound can be varied depending upon the kind of the water soluble compound. In general, it is from 5 to 95 weight percent, preferably from 10 to 90 weight percent. However, the concentration from 10 to 40 weight percent when an (a) alkylene oxide adduct of monohydric alcohols is used as (C), the concentration from 5 to 35 weight percent when a (b) monovalent salt of an organic acid or (c) lactams is used as (C), the concentration from 50 to 95 weight percent when a (d) monohydric alcohol is used as (C) and the concentration from 35 to 80 weight percent when a (e) ketone is used as (C), are especially preferable.

If the concentration of (C) is less than 5 weight percent, uniform crosslinking of the vicinity of the surface of (A) becomes difficult when (A) polysaccharide particles are treated with a (B) crosslinking agent and the aqueous solution of a (C) water soluble compound, since (A) becomes half-soluble, facilitating the aggregation of solubilized particles to easily form lumps. Further, the (B) crosslinking agent penetrates to the vicinity of the center of (A) and cause crosslinking reaction at the inside, hindering the absorbing capability. On the contrary, if the concentration exceeds 95 weight percent, a great amount of aqueous solution of (C) is needed for the treatment in order to secure sufficient water content for the crosslinking reaction to (A) and (B). Thus it is uneconomical.

In the present invention, the amount of an aqueous solution of a (C) water-soluble compound to the amount of the (A) polysaccharide particles can be varied depending upon the kind and concentration of (C), and the kind and the amount of the crosslinking agent (B). In general, it is from 1 to 10 parts by weight of aqueous solution of (C) to 100 parts by weight of (A), preferably 2 to 8 part by weight of (C) to 100 parts by weight of (A), and more preferably 2 to 5 parts by weight of (C) to 100 parts by weight of (A). If the ratio of the aqueous solution of (C) is less than 1 part by weight to 100 parts by weight of (A), uniform crosslinking reaction becomes difficult. On the contrary, if the ratio of the aqueous solution of (C) exceeds 10 parts by weight to 100 parts by weight of (A), not only does the crosslinking reaction take a longer time, but the aqueous solution of (C) penetrates to the vicinity of the center of (A) together with the (B) crosslinking agent and cause crosslinking reaction to the inside, hindering the absorbing ability.

In the present invention, to treat the (A) polysaccharide particles with the aqueous solution of the (C) water soluble compound and the (B) crosslinking agent, generally aqueous solution of (C) and (B) are mixed and then the mixture is sprayed or applied dropwise to (A) and blended afterwards. However, it is also possible that the aqueous solution of (C) and (B), without being mixed previously, are added to (A) at the same time or separately.

Conventional blenders can be used as a device for mixing (A), the aqueous solution of (C) and (B), such as a cylindrical blender, a screw blender, a screw extruder, a turbulizer, a Nauta blender, a V-shaped rotating mixer, a ribbon blender, a double arm type kneader, a fluidized bed mixer, an air blender, a rotating disc type mixer and a roll mixer.

In order to react the mixture of (A), aqueous solution of (C) and (B) obtained as mentioned above, generally heating operation is applied. Further, the above mentioned mixing and heating operations can be conducted at the same time. "The reaction" herein refers to the reaction of crosslinking the vicinity of the surface of the (A) polysaccharide particles with the (B) crosslinking agent.

For the heating operation, a drier or a heater, such as a hot-air drier, a rotary drier, a paddle drier, a rotating disc drier, a fluidized bed drier, a belt type drier, a Nauta type drier and an infrared drier can be used.

The temperature of the heating treatment varies depending upon the kind and the amount of (B), the amount of water content of the aqueous solution of (C). In general, it is 80° to 230° C., preferably 100° to 210° C. In particular, when any of ethylene glycol diglycidyl ether, propylene glycol diglycidyl ether, glycerol-1,3-diglycidyl ether, glycerol triglycidyl ether, and a polyamide polyamine epichrolhydrin resin is used as the crosslinking agent, the heating treatment can be conducted at a comparatively lower temperature, namely 100° to 180° C. A treatment temperature less than 80° C. is not so economical as it takes a long time, but also cannot advance the crosslinking reaction sufficiently to accomplish the effects of the present invention. On the other hand, a temperature exceeding 230° C. causes coloring or thermal decomposition of the absorbent, and therefore it is not preferable.

The duration of the heating treatment may be varied depending upon the kind and the amount of (B), the water content of the aqueous solution of the (C) water soluble compound, temperature of the heating treatment. In general, it is longer than 2 minutes, preferably 5 to 60 minutes. The heating time shorter than 2 minutes is not only uneconomical for the need of a higher temperature, but sometimes cannot cause crosslinking reaction sufficiently to realize the effects of the present invention according to the kind or the amount of (B).

The heating treatment can be conducted in a vacuum or an inert gas atmosphere as needed. By heating in a vacuum or an inert gas atmosphere, coloring, oxidation or heat deterioration of the absorbent can be prevented. Examples of inert gases include nitrogen, helium and carbon dioxide.

The absorbing property of an absorbent obtained in the method of the present invention can be controlled depending upon the application. The absorbing capacity against an aqueous solution of sodium chloride of 5 weight percent concentration is, in general, over 40 times, preferably over 45 times.

Accordingly, such good absorbing ability against a high concentration aqueous solution of a salt enables the use of a smaller amount compared to conventional absorbents, and thus prevents bulkiness and diminishes the cost.

To the absorbents obtained in the method of the present invention, an antiseptic agent, a fungistat, a disinfectant, an antioxidant, an ultraviolet-absorber, a coloring agent, a perfume, a deodorant, inorganic powders and an organic fibrous material can be added in case of need at an optional stage.

The present invention will be further illustrated referring to examples and comparative examples, but the present invention is not limited only to them. The absorbing capacity was measured in the method described below. Hereinafter "part" refers to part by weight and "percent" refers to weight percent.

Absorbing capacity:

1 g of an absorbent is placed in a small bag of a 250-mesh nylon net and soaked in the 5% aqueous solution of sodium chloride for 60 minutes and drained for 15 minutes. The increased weight was measured as the absorbing capacity.

EXAMPLE 1

100 parts of xanthan gum was placed in a 2,000-ml mixer and stirred with 4 parts of the aqueous solution of the crosslinking agent obtained by adding 2.5% (0.1% to xanthan gum) of ethylene glycol diglycidyl ether to the 80% aqueous solution of methanol as the (C) water soluble compound and mixed thoroughly. The obtained mixture was heated at 140° C. for approximately 20 minutes to have the absorbent (1). The absorbing capacity of the obtained absorbent (1) was measured and the measurement result is described in the Table 1.

EXAMPLE 2

In the same procedure as Example 1 except that the xanthan gum in Example 1 was replaced with the following polysaccharides, the absorbents (2) to (4) were obtained. Namely, absorbent (2) was obtained using sodium alginate, absorbent (3) was obtained using pectin, absorbent (4) was obtained using guar gum, respectively.

The absorbing capacities of the obtained absorbents (2) to (4) were measured and the measurement results are described in the Table 1.

EXAMPLE 3

In the same procedure as Example 1 except that the 80% concentration aqueous solution of methanol in Example 1 was replaced with the water soluble compounds of the kinds and concentrations as mentioned below, the absorbents (5) to (7) were obtained. Namely, absorbent (5) was obtained using 20% aqueous solution of sodium propionate, absorbent (6) was obtained using 30% aqueous solution of ethylene oxide 3 mols adduct of methanol, absorbent (7) was obtained using 20% aqueous solution of ε-caprolactam, respectively.

The absorbing capacities of the obtained absorbents (5) to (7) were measured and the measurement results are described in the Table 1.

EXAMPLE 4

In the same procedure as the Example 1 except that ethylene glycol diglycidyl ether in Example 1 was replaced with the following crosslinking agents and the temperature to heat the obtained mixture was changed to 190° C., the absorbents (8) to (10) were obtained. Namely, absorbent (8) was obtained using glycerol, absorbent (9) was obtained using polyamide polyamine epichlorohydrin resin, absorbent (10) was obtained using triethylene tetramine, respectively.

The absorbing capacities of the obtained absorbents (8) to (10) were measured and the measurement results are described in the Table 1.

EXAMPLE 5

In the same procedure as Example 1 except that 4 parts of the aqueous solution of the crosslinking agent in Example 1 was replaced with 8 parts of the aqueous solution of the crosslinking agent, the absorbent (11) was obtained. The absorbing capacity of the absorbent (11) was measured and the measurement result is described in the Table 1.

COMPARATIVE EXAMPLE 1

50 g of xanthan gum was added and dissolved in 200 ml water and subsequently 0.05 g (0.1% to xanthane gum) of ethylene glycol diglycidyl ether was added thereto and left for reaction at 40° C. for 2 hours while being stirred. The obtained reactant was dried under reduced pressure at 80° C. for 5 hours and pulverized to obtain the comparative absorbent (1) which is uniformly crosslinked to the inside of the particles.

The measurement result of the absorbing capacity of the comparative absorbent (1) measured is described in the Table 1.

COMPARATIVE EXAMPLE 2

50 g of pectin was added and dissolved in 200 ml water and subsequently 0.05 g (0.1% to pectin) of ethylene glycol diglycidyl ether was added thereto and left for reaction at 40° C. for 2 hours while being stirred. The obtained reactant was dried under reduced pressure at 80° C. for 5 hours and pulverized to obtain the comparative absorbent (2) which was uniformly crosslinked to the inside of the particles.

The measurement result of the absorbing capacity of the comparative absorbent (2) measured is described in the Table 1.

COMPARATIVE EXAMPLE 3

50 g of xanthan gum was dissolved in 500 ml water and subsequently heated at 150° C. for 2 hours with a hot air circulating drier to make the xanthan gum insoluble in water to obtain the comparative absorbent (3).

The figure of the absorbing capacity of the comparative absorbent (3) measured is described in the Table 1.

TABLE 1

|  |  | Absorbing Capacity (5% aqueous solution of sodium chloride) |
|---|---|---|
| Example 1 | Absorbent (1) | 56 |
| Example 2 | Absorbent (2) | 54 |
|  | Absorbent (3) | 56 |
|  | Absorbent (4) | 50 |
| Example 3 | Absorbent (5) | 55 |
|  | Absorbent (6) | 56 |
|  | Absorbent (7) | 53 |
| Example 4 | Absorbent (8) | 50 |

TABLE 1-continued

|  |  | Absorbing Capacity (5% aqueous solution of sodium chloride) |
|---|---|---|
|  | Absorbent (9) | 55 |
|  | Absorbent (10) | 52 |
| Example 5 | Absorbent (11) | 58 |
| Comparative | Comparative |  |
| Example | Absorbent |  |
| 1–3 | (1) | 35 |
|  | (2) | 32 |
|  | (3) | 28 |

The absorbents of the present invention have the following characteristics.

① Excellent absorbing ability to a salt water of high concentration.

② Excellent absorbing rate without liability of forming lumps at contacting a salt water.

③ The excellent absorbing ability allows the use of a smaller amount without bulkiness, enabling diminished cost when the same absorbing ability is required.

④ Comparatively good absorbing ability to an aqueous solution containing a polyvalent metal salt.

⑤ Easy disposableness after usage enabled by excellent biodegradability as mainly comprising a polysaccharide as a raw material.

The manufacturing process of the absorbents in the present invention has the below mentioned effects.

① Good operativity enabled by the fact an aqueous solution of a water soluble compound seldom solubilizes polysaccharide particles, so the polysaccharide particles seldom aggregate to form lumps in the process of treating polysaccharide particles with the aqueous solution of water soluble compound and crosslinking agent.

② Uniform and efficient crosslinking in the vicinity of the surface of the polysaccharide particles enabled by the high crosslinking concentration on the surface of the particles for the crosslinking agent not penetrating to the inside of polysaccharide particles even when the crosslinking agent is treated in the state of an aqueous solution, due to the presence of the water-soluble compound.

③ Economical for the fact that only a little amount of the aqueous solution of water-soluble compound and the crosslinking agent is needed, and the crosslinking reaction and the drying operation can be conducted at the same time.

INDUSTRIAL APPLICABILITY

For having the effects heretofore mentioned, the absorbents of the present invention can be applied broadly to the various industrial applications such as; an application for absorbing urine or blood hygienic materials such as disposable diapers, sanitary napkins, incontinence pads; an application for coagulating agents for water bearing materials containing high concentration electrolytes such as industrial sewage or undersea sludge; an application for sealing materials having high swelling property to sea water or hard water such as sealing materials for construction, mud sealing agents for shield tunneling method, water sealing materials for submarine cables; an application for curing agents after placing concrete or concrete admixture; an application for absorbents for high concentration solution of a salt for disposable hand warmers or desiccants primarily comprising calcium chloride.

We claim:

1. An absorbent having an absorbing capacity of over 40 times against an aqueous solution of sodium chloride of 5 weight % concentration, which comprises a resin obtained by reacting the surface of particles of polysaccharide (A) with a water soluble crosslinking agent (B);
   wherein said polysaccharide (A) comprises at least one selected from the group consisting of (A1) a water-soluble polysaccharide having a uronic acid group and (A2) an alkali metal salt, ammonium salt or amine salt of (A1);
   said (A1) comprising at least one selected from the group consisting of alginic acid, heparin, pectin, tragacanth gum, gum arabic and xanthan gum;
   said (B) having at least two functional groups which can react with (A) and comprising at least one compound selected from the group consisting of polyglycidyl ether compound, haloepoxy compounds, polyaldehyde compounds, polyhydric alcohol compounds, polyamine compounds and polyisocyanate compounds.

2. The absorbent according to claim 1, wherein (A1) is a polysaccharide comprising a unit component having an uronic acid group selected from the group consisting of β-D-glucuronic acid, α-L-glucuronic acid, α-D-mannuronic acid, α-D-galacturonic acid, α-L-iduronic acid and 4-0-methyl-D-glucuronic acid.

3. The absorbent according to claim 1, wherein the (B) crosslinking agent comprises at least one selected from the group consisting of polyglycidyl ether compounds, polyhydric alcohol compounds and polyamine compounds.

4. The absorbent according to claim 1, which is produced by a method comprising a step of treating the (A) polysaccharide particles with the (B) crosslinking agent and an aqueous solution of a (C) water-soluble compound.

5. The absorbent according to claim 4, wherein the ratio of (B) crosslinking agent to the (A) polysaccharide particles is 0.01 to 5 parts by weight of (B) to 100 parts by weight of (A), and the ratio of the aqueous solution of the (C) water soluble compound to the (A) polysaccharide particles is 1 to 10 parts by weight of (C) to 100 parts by weight of (A).

6. The absorbent according to claim 4, wherein the (C) water soluble compound is inert to the (A) polysaccharide particles and the (B) crosslinking agent, and comprises at least one selected from the group consisting of (a) alkylene oxide adducts of a monohydric alcohol, (b) monovalent salts of an organic acid, (c) lactams, (d) monohydric alcohols and (e) ketones.

7. The absorbent according to claim 6, wherein the water soluble compound (C) is selected from the group consisting of (a) alkylene oxide adducts of a monohydric alcohol, (b) monovalent salts of an organic acid and (c) lactams having 4–8 carbon atoms.

8. The absorbent according to claim 1, wherein the polysaccharide particles comprise xanthan gum and the crosslinking agent comprises a polyglycidyl ether compound.

* * * * *